(12) United States Patent
Hamadeh

(10) Patent No.: US 8,005,281 B2
(45) Date of Patent: Aug. 23, 2011

(54) SYSTEMS, METHODS AND APPARATUS TO DISTRIBUTE IMAGES FOR QUALITY CONTROL

(75) Inventor: Mohamed Ali Hamadeh, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 414 days.

(21) Appl. No.: 12/062,561

(22) Filed: Apr. 4, 2008

(65) Prior Publication Data

US 2009/0016581 A1 Jan. 15, 2009

Related U.S. Application Data

(62) Division of application No. 10/941,314, filed on Sep. 15, 2004, now abandoned.

(51) Int. Cl.
*G06K 9/00* (2006.01)
(52) U.S. Cl. .............................. 382/128; 128/922; 378/4
(58) Field of Classification Search .................. 382/100, 382/128, 129, 130, 131, 132, 133; 128/922; 378/4–27
See application file for complete search history.

(56) References Cited

U.S. PATENT DOCUMENTS

| 5,307,262 | A | 4/1994 | Ertel |
| 7,080,098 | B2 | 7/2006 | Smirniotopoulos et al. |
| 7,310,651 | B2 | 12/2007 | Dave et al. |
| 2001/0019587 | A1* | 9/2001 | Hashimoto et al. ...... 375/240.19 |
| 2002/0016718 | A1 | 2/2002 | Rothschild et al. |
| 2002/0042724 | A1* | 4/2002 | Victor ............................... 705/2 |
| 2002/0178031 | A1* | 11/2002 | Sorensen et al. .................. 705/2 |
| 2003/0061073 | A1* | 3/2003 | Seow et al. ....................... 705/3 |
| 2005/0196023 | A1* | 9/2005 | Chen et al. .................... 382/128 |
| 2007/0300270 | A1* | 12/2007 | Benjamin et al. ............... 725/91 |

* cited by examiner

*Primary Examiner* — Anand Bhatnagar
(74) *Attorney, Agent, or Firm* — William Baxter, Esq.; Michael G. Smith, Esq.

(57) ABSTRACT

Systems, methods and apparatus are provided through which in some embodiments an image acquisition station transmits images that have been identified as having inadequate diagnostic quality to a computer system of an image quality consultant. The image quality consultant may develop recommendations on how to improve the quality, and the recommendations are communicated to appropriate personnel.

20 Claims, 6 Drawing Sheets

SYSTEMS, METHODS AND APPARATUS TO DISTRIBUTE IMAGES FOR QUALITY CONTROL

RELATED APPLICATION

This patent application is a divisional under 35 U.S.C. 121 of U.S. patent application Ser. No. 10/941,314 filed on Sep. 15, 2004.

FIELD OF THE INVENTION

This invention relates generally to image quality review, and more particularly to a system for supporting medical image quality consultation.

BACKGROUND OF THE INVENTION

Image quality (IQ) is an important aspect of medical images. Without appropriate and satisfactory IQ, a radiologist cannot perform a reliable diagnosis using medical images. Unfortunately, some medical images may lack adequate diagnostic IQ. Causes of inadequate IQ include less than optimal acquisition parameters, patient positioning and/or image processing parameters. When such causes interfere with IQ, the radiologist may retake the images or try to reprocess the medical image using different image processing parameters until satisfactory IQ is attained.

Radiologists often consult with medical imaging engineers or IQ consultants in the analysis of medical IQ. In one such scenario of IQ consultation, a radiologist at a medical imaging facility contacts the manufacturer of the medical imaging device about inadequate IQ of one or more medical images generated by the medical imaging device. In response, the manufacturer dispatches a field engineer to the site of the medical imaging facility. The field engineer copies the medical images to a compact disk read only memory (CDROM) and sends or brings the CDROM to an IQ expert at another location, usually at a location of the manufacturer. The IQ expert examines the images on the CDROM, and communicates suggestions on changes in the acquisition parameters, patient positioning or image processing parameters.

In another consultation scenario, the radiologist at the medical imaging facility contacts the manufacturer of the medical imaging device about inadequate IQ of one or more medical images generated by the medical imaging device. In response, the manufacturer dispatches the field engineer to the site of the medical imaging facility. The field engineer contacts the manufacturer and possibly a customer support engineer at the manufacturer. In response the IQ expert and/or the customer support engineer at the manufacturer remotely accesses the images stored in an image acquisition workstation of the medical imaging device through a computer communicating over communication lines to the medical facility. The remote access is commonly referred to as insite connectivity. Thereafter, the IQ expert examines the images remotely, and communicates suggestions on changes in the acquisition parameters, patient positioning and/or image processing parameters to the medical facility.

Unfortunately, the above process of medical IQ consultation is costly and slow. The above process requires on-site visits by field engineers that cost at least hundreds of dollars in travel and personnel cost to the manufacturer, and practically speaking, at least a few hours will lapse before the medical facility will receive suggestions on changes in the acquisition parameters, patient positioning and/or image processing parameters. Often, this time delay requires a return trip by the patient to the medical facility, which further delays to acquisition of medical images with diagnostic quality.

For the reasons stated above, and for other reasons stated below which will become apparent to those skilled in the art upon reading and understanding the present specification, there is a need in the art for a system of IQ consultation that reduces the cost of the consultation to the manufacturer of the medical imaging device. There is also a need for a system of IQ consultation that reduces the amount of time required to communicate suggestions on changes in the acquisition parameters, patient positioning and/or image processing parameters, thus increasing the opportunity to finalize or complete the imaging before the patient leaves the medical facility, which in turn decreases the amount of time to obtain a image of medical diagnostic quality.

BRIEF DESCRIPTION OF THE INVENTION

The above-mentioned shortcomings, disadvantages and problems are addressed herein, which will be understood by reading and studying the following specification.

Systems, methods and apparatus are provided through which in some embodiments an image acquisition station transmits images that have been identified as having inadequate diagnostic quality to a computer system of an image quality consultant. The image quality consultant may develop recommendations on how to improve the quality, and the recommendations are communicated to appropriate personnel.

In one aspect, a system to support image quality consultation includes an imaging device that is operable to generate an electronic image of a subject, a first image-review system that is operable to receive the electronic image from the imaging device, an anonymizer of the electronic image that is operable to receive the electronic image from the first image-review system, and operable to provide access to the anonymized electronic image, and a second image-review system that is operable to receive the anonymized electronic image from the imaging device and present the anonymized electronic image.

In another aspect, the anonymized electronic image does not have the following patient information, name, birthdate, social security number, and patient number.

In yet another aspect, an online customer support system includes a receiver of an anonymized electronic image, and a transmitter of at least one recommendation on how to improve the quality of the anonymized electronic image.

In still another aspect, a human, such as a radiologist, selects an image from a graphical user interface of an image acquisition station, the image having been determined by the human as having non-diagnostic image quality, and the human selects a graphical user interface control indicating an instruction to transmit the image to an image quality consultant.

In a further aspect, a human image quality consultant receives notice of receipt by a image-review system of an anonymized electronic image for image quality consultation, the consultant analyzes the anonymized image for recommendations on how to improve the quality of the anonymized electronic image, and communicates the recommendations to an image technician.

Systems, clients, servers, methods, and computer-readable media of varying scope are described herein. In addition to the aspects and advantages described in this summary, further aspects and advantages will become apparent by reference to the drawings and by reading the detailed description that follows.

By providing electronic access to diagnostic images that have non-diagnostic image quality by the image quality consultant expert in the automated manner of system with fewer intervening actions than conventional systems, such as dispatching a field engineer, valuable advice is provided to the medical image technician on how to improve the quality of those diagnostic images in more timely manner. The image quality consultant expert, upon reviewing the anonymized images can assess the situation and provide a set of recommendations/solutions to the medical image technician in a more timely manner. Hence, the medical facility who can attain diagnostic image quality of medical images by following the recommendations in a more timely manner.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, methods of embodiments are described. In the third section, the hardware and the operating environment in conjunction with which embodiments may be practiced are described. In the fourth section, particular implementations are described. Finally, in the fifth section, a conclusion of the detailed description is provided.

System Level Overview

Figure 1:
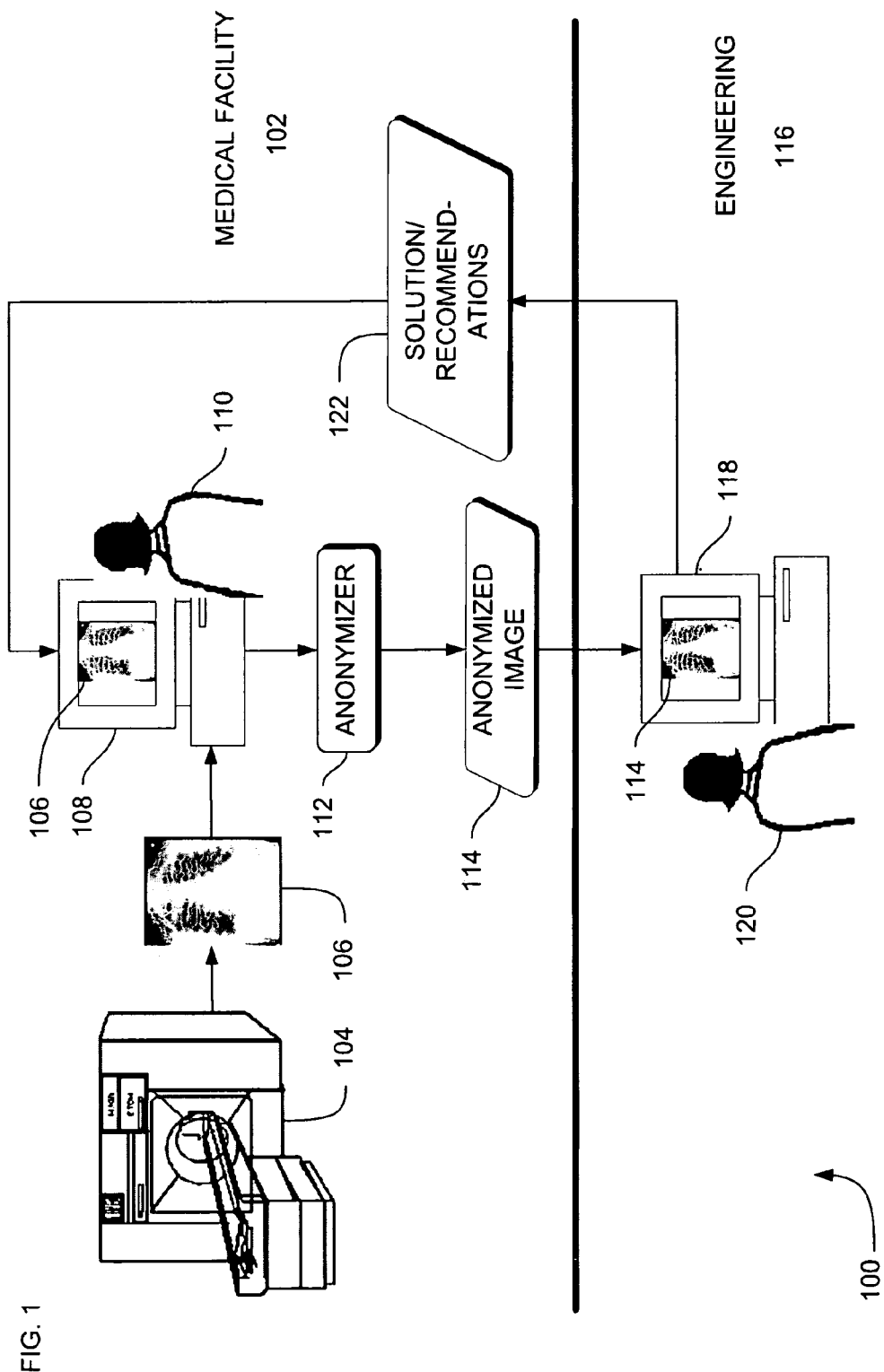
FIG. 1 is a diagram illustrating a system-level overview of an embodiment.

FIG. 1 is a block diagram that provides a system level overview of a system to support image quality consultation. System solves the need in the art for reduced time and cost in medical IQ consultation.

In system 100, some embodiments of a medical facility 102 include an imaging device 104 that is operable to generate an electronic image 106 of a subject (not shown). Examples of imaging devices include magnetic resonance (MR) imaging devices, computed tomography (CT) devices, ultrasound imaging devices, and X-ray devices.

Some embodiments of system 100 include a first image-review system 108 in the medical facility 102 that is operable to receive the electronic image 106 from the imaging device 104. The first image-review system 108 displays the electronic image 106. A medical image technician 110 reviews the electronic image 106 determines that the consultation of an image quality consultant would be helpful in review of the electronic image 106. In some embodiments, the first image-review system 108 is an image acquisition workstation. In some embodiments, the medical image technician 110 is a radiologist or another worker on the medical staff of the medical facility 102.

Some embodiments of system 100 also include an anonymizer 112 of the electronic image. The anonymizer 112 is operable to receive the electronic image 106 from the first image-review system 108, and operable to provide access to the anonymized electronic image 114. The anonymizer creates a version of the electronic image 106 that limited to including anonymous information on the patient subject of the electronic image 106. The anonymized electronic image 114 excludes information that could identify the patient subject; that information includes the name, social security numbers, address and patient number of the patient subject. The anonymization of the electronic image 106 protects the privacy of the patient from any misuse, such as identity theft, of confidential information.

In some embodiments of system 100, in an engineering facility 116, the anonymized electronic image 114 is received by a second image-review system 118 and the anonymized electronic image 114 is displayed by the second image-review system 118 for review and analysis by an image quality consultant 120. The anonymization of the electronic image 106 protects the engineering facility 116 from any misuse, such as identity theft, of the confidential information.

The image quality consultant 120 communicates solutions, recommendations and/or advice 122 to the medical image technician 110 on how to improve the quality of the anonymized electronic image 114 or how to image the subject again under different circumstances of optimal acquisition parameters, patient positioning and/or image processing parameters that are reasonably calculated to yield an image with improved quality in comparison to the anonymized electronic image. 114.

By providing electronic access to diagnostic images that have non-diagnostic IQ by the image quality consultant 120 expert in the automated manner of system 100 with fewer intervening actions than conventional systems, such as dispatching a field engineer, valuable advice is provided to the medical image technician 110 on how to improve the quality of those diagnostic image 114 in more timely manner. The image quality consultant 120 expert, upon reviewing the anonymized images can assess the situation and provide a set of recommendations/solutions 122 to the medical image technician 110 in a more timely manner. Hence, the medical facility 102 can attain diagnostic IQ of medical images by following the recommendations 122 in a more timely manner.

Thus, system 100 reduces the cost of the consultation to the manufacturer of the medical imaging device 104 by reducing the need to dispatch a field engineer to the medical facility 102. System 100 also reduces the amount of time required to communicate suggestions on changes in the acquisition parameters, patient positioning in imaging device 104 and/or image processing parameters, which in turn increases the opportunity to finalize or complete the imaging before the patient leaves the medical facility 102, which in turn decreases the amount of time to obtain an image of medical diagnostic quality.

The system level overview of the operation of an embodiment has been described in this section of the detailed description. Some embodiments operate in a multi-processing, multi-threaded operating environment on a computer, such as computer 402 in FIG. 4.

While the system 100 is not limited to any particular medical facility 102, imaging device 104, electronic image 106, image-review system 108, medical image technician 110, anonymizer 112, anonymized electronic image 114, engineering facility 116, image-review system 118, image quality consultant 120 and solutions, recommendations and/or advice 122, for sake of clarity simplified medical facility 102, imaging device 104, electronic image 106, image-review system 108, medical image technician 110, anonymizer 112, anonymized electronic image 114, engineering facility 116, image-review system 118, image quality consultant 120 and solutions, recommendations and/or advice 122 have been described.

Methods of an Embodiment

In the previous section, a system level overview of the operation of an embodiment was described. In this section, the particular methods performed by the server and the clients of such an embodiment are described by reference to a series of flowcharts. Describing the methods by reference to a flowchart enables one skilled in the art to develop such programs, firmware, or hardware, including such instructions to carry out the methods on the processor of the clients and servers executing the instructions from computer-readable media. Similarly, the methods performed by the server computer programs, firmware, or hardware are also composed of computer-executable instructions. Methods 200-300 are performed by computer instructions executing on, or performed by firmware or hardware that is a part of, a computer, such as computer 402 in FIG. 4.

Figure 2:
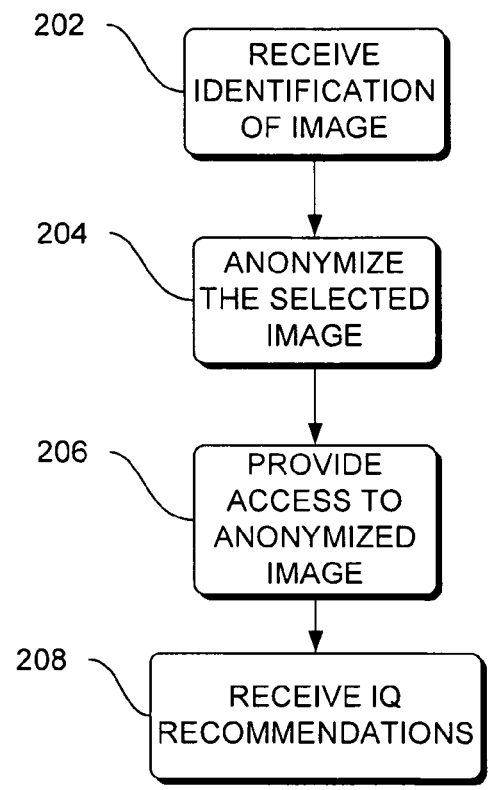
FIG. 2 is a flowchart of a method performed by an acquisition workstation according to an embodiment.

FIG. 2 is a flowchart of a method 200 performed by an acquisition workstation according to an embodiment. Method 200 solves the need in art for reduced time and cost in medical IQ consultation.

Method 200 includes receiving 202 an identification of one or more images 106 to be accessed by an engineering image quality (IQ) expert, such as IQ expert 120 in FIG. 1. In some embodiments, one or more of the identified images includes annotations in images or associated with the images that indicate particular problems with the IQ. The annotations are typically added by the medical image technician 110 as an aid to the analysis of the IQ problems by the image quality consultant 120.

In some embodiments, the identification is prompted by a user of an image presentation program in which the user selects images in any one of a number of conventional graphical user interface techniques, such as by clicking a radio button or a button associated with an image or selecting a option from a pull-down menu that indicates selection of an image.

In some embodiments, method 200 includes receiving (not shown) an affirmation of transmission of the one or more selected images to an image quality consultant. In some embodiments, the affirmation is prompted by a user of an image presentation program in which the user selects images in any one of a number of conventional graphical user interface techniques, such as by clicking a radio button associated with an image or selecting a option from a pull-down menu that indicates affirmation of transmission of the one or more selected image to an image quality consultant.

Thereafter, the one or more identified images are anonymized 204 in some embodiments. In some embodiments, anonymizing 204 includes removing or deleting confidential personal information of the patient subject of the image(s) in order to protect confidentiality of the patient subject. In some embodiments, anonymizing 204 is performed by anonymizer 112 in FIG. 1.

Thereafter, method 200 includes providing 206 access of the anonymized image(s), such as image 114, to the IQ expert 120. In some embodiments, access is provided by sending, transmitting and/or pushing the anonymized image(s) to a computer system, such as image-review system 118 in FIG. 1, to which the IQ expert 120 has access. In these embodiments, an electronic communication session is initiated with an Engineering IQ expert. Such communication is generic and can be dependent on the medical facility and/or the Engineering department policies. One example for such communication initiation can be handled via an On Line Center support that will in this case provide a communication bridge between the site and the engineering department.

Either of the electronic image 106 or the anonymized image 114 may be encoded in some embodiment in accordance with a conventional graphic encoding scheme such as JPEG, GIF, TIFF, BMP, PCX, TGA, PNG, SVG, ANALYZE (published by the Mayo Clinic of Rochester, Minn.), MINC, AFNI, MPEG and Quicktime. In some embodiments, the electronic image 106 is encapsulated in an image annotation object (not shown) that conforms to an image annotation standard, such as DICOM, the Papyrus standard published by the the Numerical Unit of Imagery in France (based on DICOM), General Electric MRI/LX, General Electric MRI/Genesis 5, General Electric MRI/Signa, General Electric Scanditronix (4096 PET format), and Interfile published by the Society of Nuclear Medicine in Reston, Va.

DICOM (Digital Imaging and Communications in Medicine) standard 3.0 defines twenty-four data elements in object-oriented terms. Each DICOM object has a unique tag, name, characteristics and semantics. DICOM requires conformance statements that identify de minimus data requirements. DICOM conforms to the International Organization for Standardization (ISO) reference model for network communications. The DICOM standard was developed jointly by the National Equipment Manufacturers Association (NEMA) in Rosslyn, Va. and by the American College of Radiology (ACR). DICOM is published by NEMA. The DICOM standard is also known as the ACR/NEMA standard.

In some embodiments, method 200 further includes receiving 208 IQ recommendations, such as recommendation 122 in FIG. 1. Receiving 208 the recommendations 122 can be performed by a variety of manners, such as the acquisition workstation 108 receiving the recommendations 122 in an electronic format through an electronic communication channel (e.g. email through the Internet or an online customer support system) as shown in FIG. 1. In another manner of receiving 208, a medical image technician 110 at the medical facility 102 receives the recommendations 122 via telephone or facsimile transmission from the IQ expert 120 or a field engineer.

Figure 3:
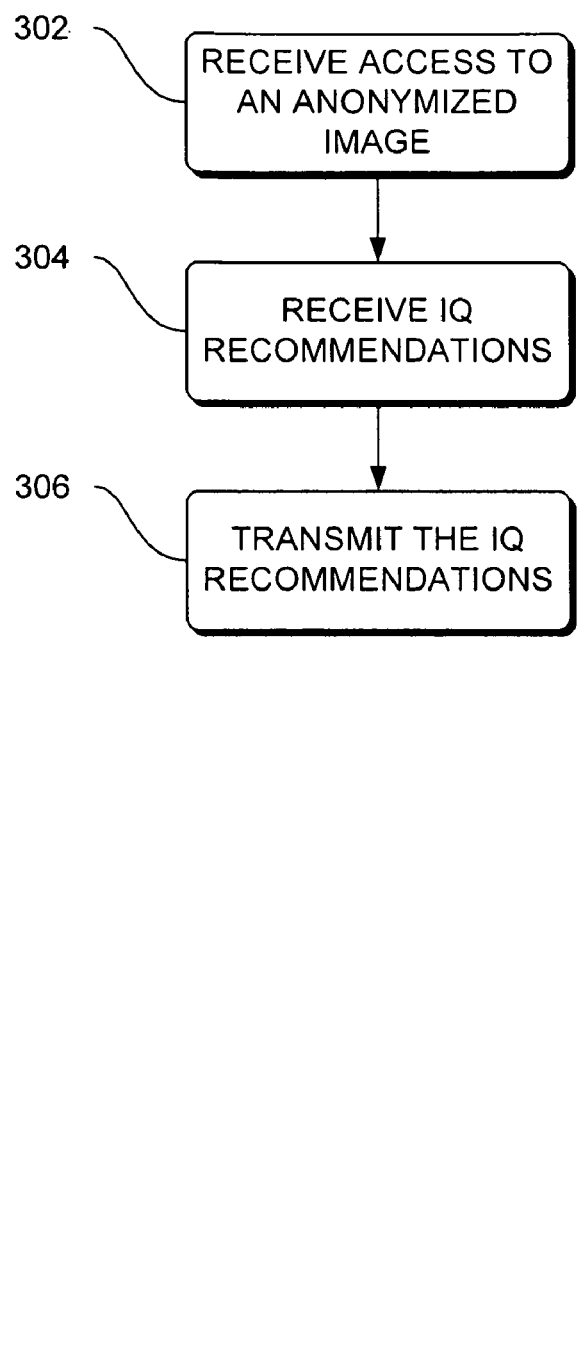
FIG. 3 is a flowchart of a method to support image quality consultation by a manufacturer of a medical imaging device.

FIG. 3 is a flowchart of a method 300 to support image quality consultation by a manufacturer of a medical imaging device, performed by an image-review system according to an embodiment. Method 300 solves the need in art for reduced time and cost in medical IQ consultation. One example of an image-review system is image-review system 118 in FIG. 1.

In some embodiments, method 200 includes receiving 302 access to at least one anonymized image. In some examples, the anonymized image 114 in FIG. 1 that is generated by the anonymizer 112 in action 204 of FIG. 2. The anonymized image contains no information that could be used to ascertain the identity of the patient in the image. In some embodiments when access is received or the anonymized image is received, an associated IQ expert is notified immediately.

In some embodiments, method 200 also includes receiving 304 recommendations of image quality (IQ) consultation of the anonymized image. The recommendations are typically created by an image quality consultant 120 in FIG. 1.

In some embodiments, method 300 thereafter includes transmitting 306 the recommendations. The recommendations are transmitted in the same variety of manners as in action 208 in FIG. 2, such as the image-review system transmitting the recommendations to a acquisition workstation in an electronic format through an electronic communication channel (e.g. email through the Internet or an online customer support system) as shown in FIG. 1, and/or the IQ consultant 120 communicating the recommendation to the medical image technician 110 at the medical facility 102 via telephone or facsimile transmission from the IQ expert 120 or a field engineer.

Figure 4:
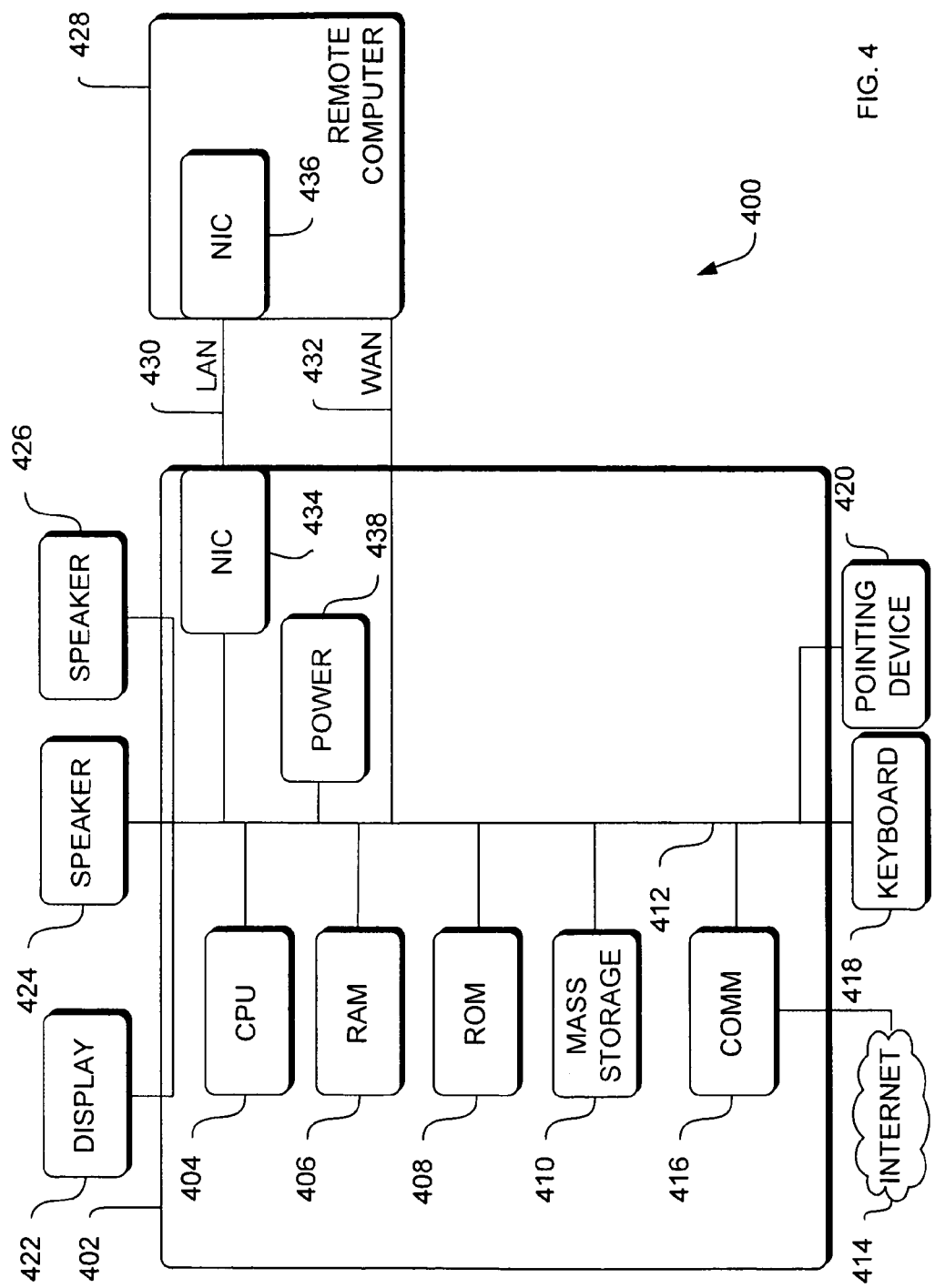
FIG. 4 is a block diagram of the hardware and operating environment in which different embodiments can be practiced.

In some embodiments, methods 200-300 are implemented as a computer data signal embodied in a carrier wave, that represents a sequence of instructions which, when executed by a processor, such as processor 404 in FIG. 4, cause the processor to perform the respective method. In other embodiments, methods 200-300 are implemented as a computer-accessible medium having executable instructions capable of directing a processor, such as processor 404 in FIG. 4, to perform the respective method. In varying embodiments, the medium is a magnetic medium, an electronic medium, or an optical medium.

Hardware and Operating Environment

FIG. 4 is a block diagram of the hardware and operating environment 400 in which different embodiments can be practiced. The description of FIG. 4 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 402 includes a processor 404, commercially available from Intel, Motorola, Cyrix and others. Computer 402 also includes random-access memory (RAM) 406, read-only memory (ROM) 408, and one or more mass storage devices 410, and a system bus 412, that operatively couples various system components to the processing unit 404. The memory 406, 408, and mass storage devices, 410, are types of computer-accessible media. Mass storage devices 410 are more specifically types of nonvolatile computer-accessible media and can include one or more hard disk drives, floppy disk drives, optical disk drives, and tape cartridge drives. The processor 404 executes computer programs stored on the computer-accessible media.

Computer 402 can be communicatively connected to the Internet 414 via a communication device 416. Internet 414 connectivity is well known within the art. In one embodiment, a communication device 416 is a modem that responds to communication drivers to connect to the Internet via what is known in the art as a "dial-up connection." In another embodiment, a communication device 416 is an Ethernet® or similar hardware network card connected to a local-area network (LAN) that itself is connected to the Internet via what is known in the art as a "direct connection" (e.g., T1 line, etc.).

A user enters commands and information into the computer 402 through input devices such as a keyboard 418 or a pointing device 420. The keyboard 418 permits entry of textual information into computer 402, as known within the art, and embodiments are not limited to any particular type of keyboard. Pointing device 420 permits the control of the screen pointer provided by a graphical user interface (GUI) of operating systems such as versions of Microsoft Windows®. Embodiments are not limited to any particular pointing device 420. Such pointing devices include mice, touch pads, trackballs, remote controls and point sticks. Other input devices (not shown) can include a microphone, joystick, game pad, satellite dish, scanner, or the like.

In some embodiments, computer 402 is operatively coupled to a display device 422. Display device 422 is connected to the system bus 412. Display device 422 permits the display of information, including computer, video and other information, for viewing by a user of the computer. Embodiments are not limited to any particular display device 422. Such display devices include cathode ray tube (CRT) displays (monitors), as well as flat panel displays such as liquid crystal displays (LCD's). In addition to a monitor, computers typically include other peripheral input/output devices such as printers (not shown). Speakers 424 and 426 provide audio output of signals. Speakers 424 and 426 are also connected to the system bus 412.

Computer 402 also includes an operating system (not shown) that is stored on the computer-accessible media RAM 406, ROM 408, and mass storage device 410, and is and executed by the processor 404. Examples of operating systems include Microsoft Windows®, Apple MacOS®, Linux®, UNIX®. Examples are not limited to any particular operating system, however, and the construction and use of such operating systems are well known within the art.

Embodiments of computer 402 are not limited to any type of computer 402. In varying embodiments, computer 402 comprises a PC-compatible computer, a MacOS®-compatible computer, a Linux®-compatible computer, or a UNIX®-compatible computer. The construction and operation of such computers are well known within the art.

Computer 402 can be operated using at least one operating system to provide a graphical user interface (GUI) including a user-controllable pointer. Computer 402 can have at least one web browser application program executing within at least one operating system, to permit users of computer 402 to access an intranet, extranet or Internet world-wide-web pages as addressed by Universal Resource Locator (URL) addresses. Examples of browser application programs include Netscape Navigator® and Microsoft Internet Explorer®.

The computer 402 can operate in a networked environment using logical connections to one or more remote computers, such as remote computer 428. These logical connections are achieved by a communication device coupled to, or a part of, the computer 402. Embodiments are not limited to a particular type of communications device. The remote computer 428 can be another computer, a server, a router, a network PC, a client, a peer device or other common network node. The logical connections depicted in FIG. 4 include a local-area network (LAN) 430 and a wide-area network (WAN) 432. Such networking environments are commonplace in offices, enterprise-wide computer networks, intranets, extranets and the Internet.

When used in a LAN-networking environment, the computer 402 and remote computer 428 are connected to the local network 430 through network interfaces or adapters 434, which is one type of communications device 416. Remote computer 428 also includes a network device 436. When used in a conventional WAN-networking environment, the computer 402 and remote computer 428 communicate with a WAN 432 through modems (not shown). The modem, which can be internal or external, is connected to the system bus 412. In a networked environment, program modules depicted relative to the computer 402, or portions thereof, can be stored in the remote computer 428.

Computer 402 also includes power supply 438. Each power supply can be a battery.

Acquisition Workstation Implementation

Figure 5:
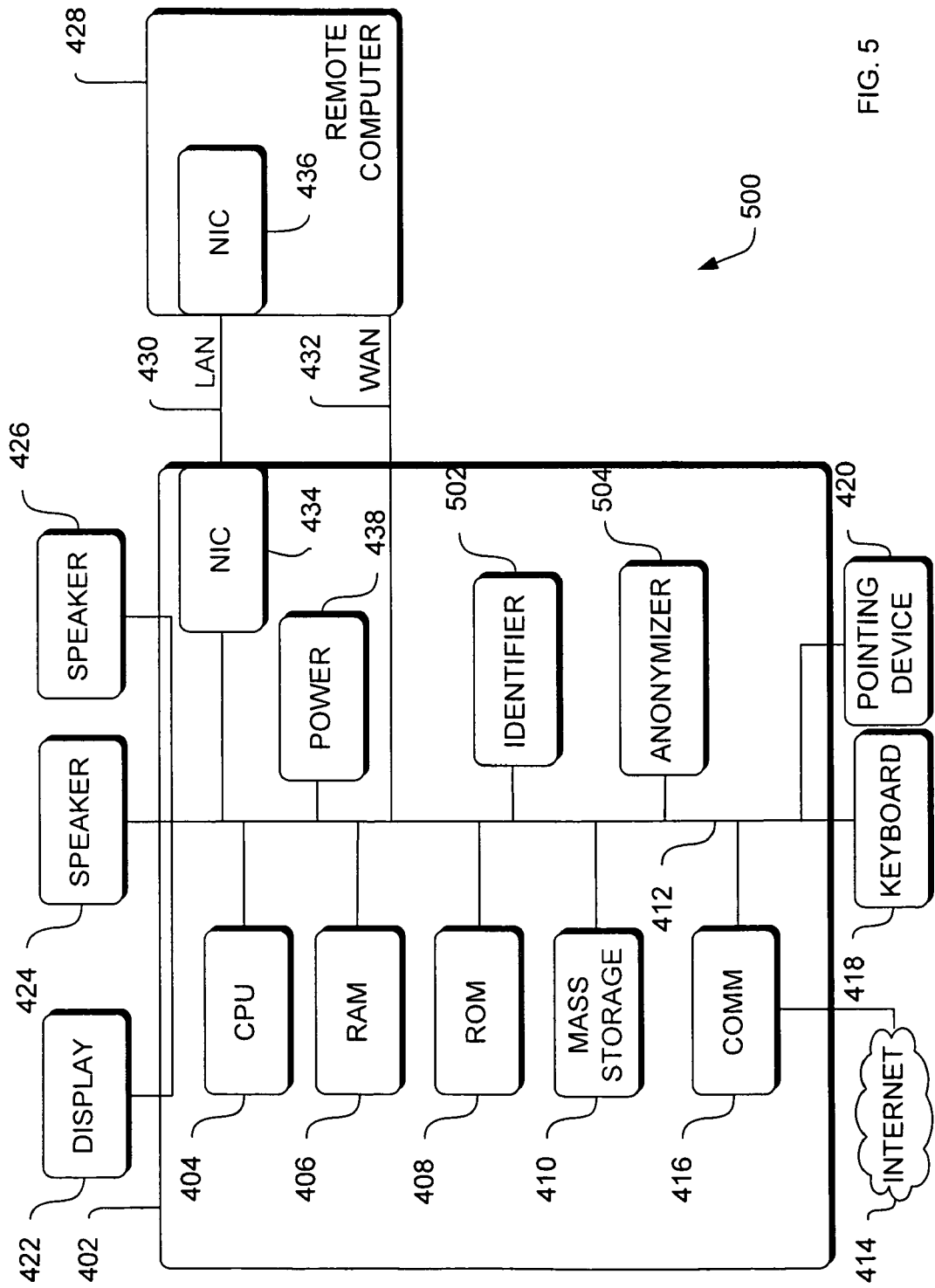
FIG. 5 is a block diagram of a particular implementation of an acquisition workstation.

Referring to FIG. 5, a particular implementation of an acquisition workstation 500 is described in conjunction with the system overview in FIG. 1 and the methods described in conjunction with FIGS. 2 and 3.

Apparatus 500 includes an identifier 502 of one or more images, such as image 106 in FIG. 1, to be accessed by an engineering image quality (IQ) expert, such as IQ expert 120 in FIG. 1. In some embodiments, the identification is prompted by a user of an image presentation program (not shown) in which the user selects images in any one of a number of conventional graphical user interface means displayed on display 422, such as by clicking a radio button associated with an image or selecting a option from a pull-down menu that indicates selection of an image.

Apparatus 500 also includes an anonymizer 504, such as anonymizer 112 in FIG. 1. The anonymizer 504 is operable to remove confidential patient information from the electronic image identified by identifier 502. In some embodiments, the anonymizer accesses the identified image in reference to the identification generated by the identifier. In some embodiments, the anonymizer receives the identified image from the identifier 502.

Apparatus 500 components of the identifier 502 and the anonymizer 504 can be embodied as computer hardware circuitry or as a computer-readable program, or a combination of both. In another embodiment, the identifier 502 and/or the anonymizer 504 are implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 402 in FIG. 4, or on at least as many computers as there are components.

Figure 6:
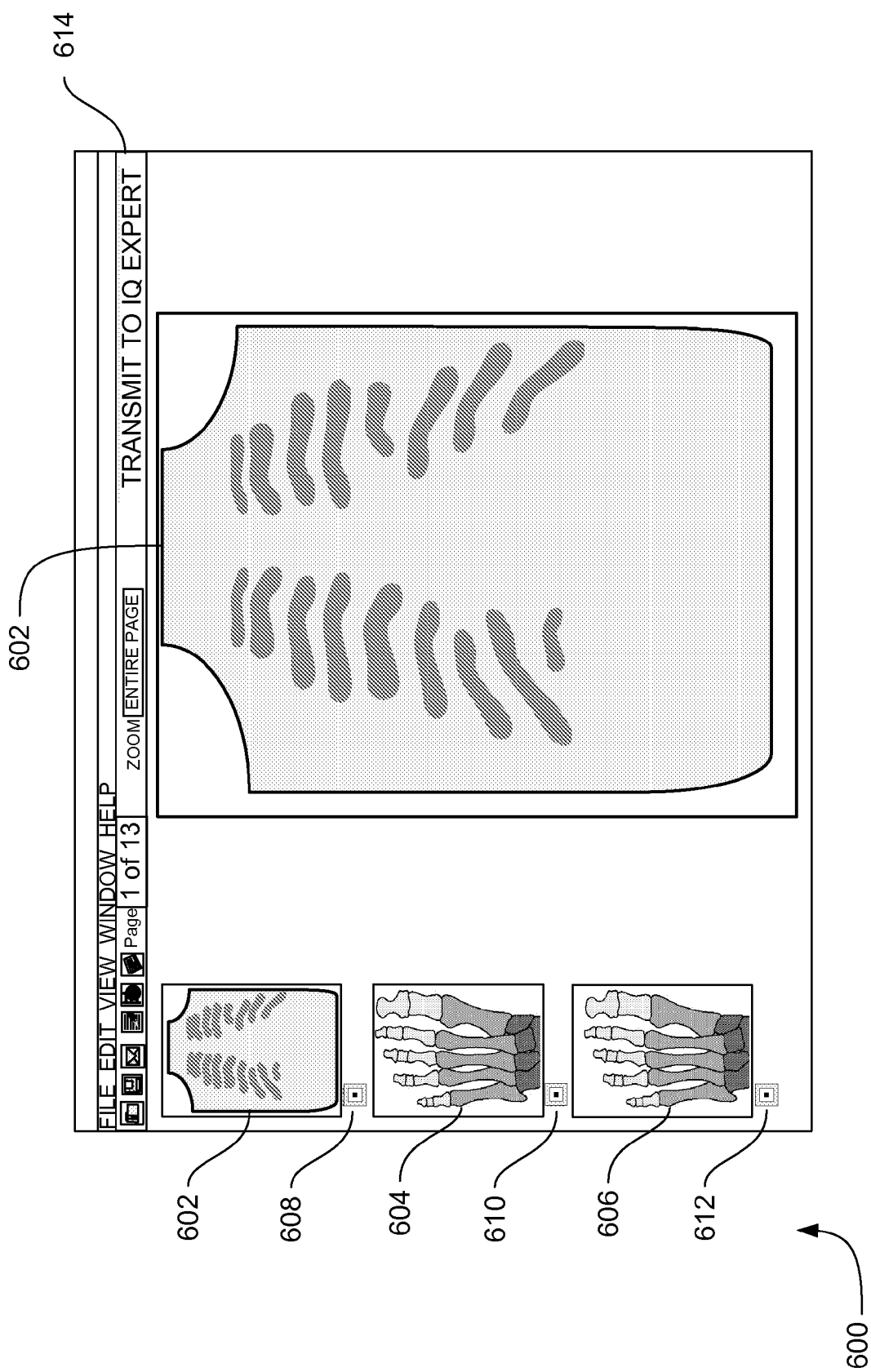
FIG. 6 is a diagram of a graphical user interface in which different embodiments can be practiced.

FIG. 6 is a diagram of a graphical user interface (GUI) 600 in which different embodiments can be practiced.

GUI 600 displays medical images 602, 604 and 606. For each image, the GUI 600 includes a graphical region associated with the image that is operable to indicate that the associated image is selected. Examples of the graphical regions include a radio button, a button and an item in a pull-down menu. In GUI 600, radio buttons 608, 610 and 612 are operable to indicate selected images 602, 604 and 606 respectively. More specifically, radio buttons 608 and 612 indicate that images 602 and 606 are selected, respectively.

GUI 600 includes a graphical region 614 that is operable to indicate an affirmation of transmission of the at least one selected image to an image quality consultant. In the embodiment shown in GUI 600, the graphical region 614 is a button.

CONCLUSION

An image quality analysis system has been described. In some embodiments, the method/workflow is entirely automated. In fact, all the radiologist needs to do is to select the images to be sent to the IQ expert and launches the specific application that will anonymize the images and send them automatically to the IQ expert. The IQ expert assigned to this medical facility will be immediately notified that the IQ expert has a case of IQ to assess and investigate in order to respond to the radiologist and give him the recommended solution.

The systems, methods and apparatus described herein provide the following advantages: Avoids retake of medical images when image quality can be recovered or improved using image-processing techniques, provides faster response from engineering to address image quality issues encountered on sites, enhances IQ engineering expertise: When exposed to diverse issues regarding image quality, the IQ expert can establish some common pattern of problems and their solutions. A database of encountered IQ issues is an excellent source of information for engineering to address and resolve in future programs and new product introductions.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application is meant to include all object-oriented, database and communication environments and alternate technologies which provide the same functionality as described herein.

I claim:

1. A method to support image quality consultation, the method comprising:
receiving to a memory an identification of an X-ray image to be transmitted to an online customer support system of a manufacturer that is associated with an engineering image quality expert;
anonymizing the identified X-ray image in the memory; and transmitting the anonymized image from the memory to the online customer support system.

2. The method of claim 1 further comprising
providing access from the memory by an engineering image quality expert to the anonymized image; and
receiving recommendations to the memory of image quality consultation from the engineering image quality expert in reference to the anonymized image.

3. The method of claim 2, wherein identification further comprises:
an identification performed by a medical imaging technician.

4. The method of claim 2, wherein providing access to the anonymized image further comprises:
transmitting the anonymized image from the memory to the manufacturer of the imaging device that generated the anonymized image.

5. The method claim of 2, wherein anonymized image in the memory does not have the following patient information; name, birthdate, social security number, and patient number.

6. The method of claim 2, wherein each of the recommendations in the memory further comprise:
at least one recommendation on how to image a subject of the anonymized image again under different circumstances of optimal acquisition parameters, patient positioning and/or image processing parameters that are reasonably calculated to yield an image with improved quality in comparison to the electronic image.

7. The method of claim 1 further comprising
transmitting the anonymized image from the memory to the manufacturer of the imaging device that generated the electronic image; and
receiving to the memory recommendations of an image quality consultation in reference to the anonymized image.

8. The method of claim 7, wherein identification further comprises:
an identification performed by a medical imaging technician.

9. The method of claim 7, wherein confidential patient information further comprise; name, birthdate, social security number, and patient number.

10. The method of claim 7, wherein each of the recommendations further comprise:
at least one recommendation on how to image a subject of the electronic image again under different circumstances of optimal acquisition parameters, patient positioning and/or image processing parameters that are reasonably calculated to yield an image with improved quality in comparison to the electronic image.

11. The method of claim 7, wherein the medical electronic imaging device further comprises:
a magnetic resonance imaging device.

12. The method of claim 1 further comprising:
receiving to the memory at least one recommendation of image quality consultation in reference to the anonymized image from the online customer support system.

13. The method of claim 12, wherein the at least one recommendation further comprises:
at least one recommendation on how to image the subject again under different circumstances of optimal acquisition parameters, patient positioning and/or image processing parameters that are reasonably calculated to yield an image with improved quality in comparison to the electronic image.

14. The method of claim 1, wherein the identification further comprises:
an identification performed by a medical imaging technician in the memory.

15. The method of claim 1 further comprising:
receiving in the memory, recommendations of image quality consultation of the anonymized image.

16. The method of claim 15, wherein the receiving further comprises:
receiving the recommendations from an engineering image quality expert.

17. The method of claim 15, wherein each of the recommendations in the memory further comprise:
a recommendation on how to improve the quality of the electronic image.

18. The method of claim 15, wherein the transmitting is performed through the Internet.

19. The method of claim 15, wherein anonymized image does not have the following patient information; name, birthdate, social security number, and patient number.

20. The method of claim 15, wherein each of the recommendations in the memory further comprise:
at least one recommendation on how to image a subject of the at least one image again under different circumstances of optimal acquisition parameters, patient positioning and/or image processing parameters that are reasonably calculated to yield an image with improved quality in comparison to the electronic image.

* * * * *